United States Patent [19]

Burnier et al.

[11] Patent Number: 4,835,251

[45] Date of Patent: May 30, 1989

[54] METHOD OF CHAIN COMBINATION

[75] Inventors: John P. Burnier, Pacifica; Paul D. Johnston, San Bruno, both of Calif.

[73] Assignee: Genetech, Inc., South San Francisco, Calif.

[21] Appl. No.: 877,819

[22] Filed: Jun. 23, 1986

[51] Int. Cl.⁴ .............................................. C07K 7/10
[52] U.S. Cl. .................................. 530/324; 530/333
[58] Field of Search ............................... 530/324, 333

[56] References Cited

U.S. PATENT DOCUMENTS

| | | | |
|---|---|---|---|
| 4,421,685 | 12/1983 | Chance | 260/112.7 |
| 4,656,249 | 4/1987 | Florey | 530/324 |
| 4,758,516 | 7/1988 | Hudson et al. | 536/27 |

FOREIGN PATENT DOCUMENTS

| | | |
|---|---|---|
| 6884481 | 10/1981 | Australia . |
| 0037256 | 10/1981 | European Pat. Off. . |
| 101309 | 2/1984 | European Pat. Off. . |
| 112149 | 6/1984 | European Pat. Off. . |

OTHER PUBLICATIONS

Chance et al., Peptides, Synthesis-Structure-Function, Rich and Gross, eds., Rockford, Pierce Chemical Co. Press, pp. 721-728 (1981).
Johnston et al., Ninth American Peptide Symposium, Abstracts, Jun. 23-28, 1985, P-MTu-118, p. 109.
Johnston et al., Ninth American Peptide Symposium, Poster, Jun. 23-28, 1985.
Tregear et al., Biology of Relaxin and Its Role in the Human, Bigazzi et al., Eds., Proceedings of the 1st International Conference on Human Relaxin, Florence, Sep. 30-Oct. 2, 1982, pp. 42-55.
Blundell, T. et al., in *Biology of Relaxin and Its Role in the Human*, (Exc. Med., Amster.) pp. 14-21, Bigazzi, et al. (eds) 1983.
Busse, W. D. and Carpenter, F. H. *Biochemistry*, 15: 1649-1657 (1976).
Hudson P. et al., *The EMBO Journal*, 3: 2333-2339 (1984).
Hudson, P. et al., *Nature*, 301: 628-631 (1983).
James, R. et al., *Nature*, 267: 544 (1977).
Johnston, P. D. et al., in *Peptides: Structure & Function, Proc. 9th American Peptide Sympos.* (Pierce Chem. Co.), Deber et al. (ed) 1985.
Katsoyannis, P. G. et al., *Biochemistry*, 6: 2656-2668 (1967).
Schwabe, C. and McDonald, J. R., *Science* 197: 914-915 (1977).
Tregear, G. et al., in Relaxin; (Elsevier, N.Y.), Bryant--Greenwood et al. (eds), 1981, pp. 151-164 "The Synthesis of Peptides with Relaxin Activity".
Kung et al., *Scientia Sinica*, 15: 544 (1966).

*Primary Examiner*—Delbert R. Phillips
*Attorney, Agent, or Firm*—Janet E. Hasak

[57] ABSTRACT

Production of human relaxin or novel human relaxin analogs by combination of a human relaxin A-chain and B-chain comprises combining the reduced form of the human relaxin A-chain and the reduced form of the human relaxin B-chain in an aqueous medium having a pH of about 7.0 to 12 at room temperature, under conditions that are mildly denaturing for the relaxin B-chain such that the human relaxin or novel human relaxin analog can be formed.

20 Claims, 6 Drawing Sheets

Fig. 1.

|  | B-chain |
|---|---|
| HUMAN INSULIN | Ala Ala Ala Phe Val Asn Gln His Leu Cys Gly Ser His |
| HUMAN RELAXIN-1 | Ala Val Ala Ala Lys Trp Lys Asp Asp Val Ile Lys Leu Cys Gly Arg Glu |
| HUMAN RELAXIN-2 | Ala Val Ala Asp Ser Trp Met Glu Glu Val Ile Lys Leu Cys Gly Arg Glu |
| PORCINE RELAXIN | Gln Ser Thr Asn Asp Phe Ile Lys Ala Cys Gly Arg Glu |
| RAT RELAXIN | Arg Val Ser Glu Glu Trp Met Asp Gln Val Ile Gln Val Cys Gly Arg Gly |
| SHARK RELAXIN | Gln Ser Leu Ser Asn Ala Gly Ser Gly Ile Lys Leu Cys Gly Arg Gly |
| DOGFISH RELAXIN | Gln Asn Ala Glu Pro Gly Ile Lys Leu Cys Gly Arg Glu |

|  | A-chain |
|---|---|
| HUMAN INSULIN | Lys Arg Gly Ile Val Glu Gln Cys Cys Thr Ser Ile |
| HUMAN RELAXIN-1 | Lys Lys Arg Arg Pro Tyr Val Ala Leu Phe Glu Lys Cys Cys Leu Ile Gly |
| HUMAN RELAXIN-2 | Lys Lys Arg Gln Leu Tyr Ser Ala Leu Ala Asn Lys Cys Cys His Val Gly |
| PORCINE RELAXIN | Lys Lys Arg Leu Phe Arg Met Thr Leu Ser Glu Lys Cys Cys Gln Val Gly |
| RAT RELAXIN | Lys Lys Arg Gln Ser Gly Ala Leu Leu Ser Glu Gln Lys Cys Cys His Ile Gly |
| SHARK RELAXIN | Ala Thr Ser Pro Ala Met Ser Ile Lys Cys Cys Ile Tyr Gly |
| DOGFISH RELAXIN | Glu Gly Ser Pro Gly Met Ser Ser Lys Cys Cys Thr Tyr Gly |

Fig.1.(cont.)

| | | | | | | | | | | | | | | | |
|---|---|---|---|---|---|---|---|---|---|---|---|---|---|---|---|
| Leu | Val | Glu | Ala | Leu | Tyr | Leu | Val | Cys | Gly | Glu | Arg | Gly | Phe | Phe | Tyr | Thr | Pro | lys | Thr | Arg | Arg |
| | | | | | | 20 | | | | | | | | | 30 | | | | | | |
| Leu | Val | Arg | Ala | Ala | Gln | Ile | Ala | Ile | Cys | Gly | Met | Ser | Thr | Trp | Ser | Lys | Arg | Ser | Leu | Ser | Gln |
| Leu | Val | Arg | Ala | Ala | Gln | Ile | Ala | Ile | Cys | Gly | Met | Ser | Thr | Trp | Ser | Lys | Arg | Ser | Leu | Ser | Gln |
| Leu | Val | Arg | Leu | Trp | Val | Glu | Ile | Cys | Gly | Ser | Val | Ser | Trp | Gly | Arg | Thr | Ala | Leu | Ser | Leu | |
| Tyr | Ala | Arg | Ala | Trp | Ile | Glu | Val | Cys | Gly | Ala | | Ser | Val | Gly | Arg | Leu | Ala | Leu | Ser | Gln | |
| Phe | Ile | Arg | Ala | Ile | Phe | Ala | Cys | Gly | Ser | Arg | | | | | | | | | | | |
| Phe | Ile | Arg | Ala | Val | Ile | Tyr | Ser | Cys | Gly | | | | | | | | | | | | |
| Cys | Ser | Leu | Tyr | Gln | Leu | Glu | Asn | Tyr | Cys | Asn | | | | | | | | | | | |
| | | | | | | 20 | | | | | | | | | | | | | | | |
| Cys | Thr | Lys | Arg | Ser | Leu | Ala | Lys | Tyr | Cys | | | | | | | | | | | | |
| Cys | Thr | Lys | Arg | Ser | Leu | Ala | Arg | Phe | Cys | | | | | | | | | | | | |
| Cys | Ile | Arg | Lys | Asp | Ile | Ala | Arg | Leu | Cys | | | | | | | | | | | | |
| Cys | Thr | Arg | Ser | Ile | Ala | Lys | Leu | Cys | | | | | | | | | | | | | |
| Cys | Thr | Lys | Asp | Ile | Ser | Val | Leu | Cys | | | | | | | | | | | | | |
| Cys | Thr | Arg | Lys | Asp | Ile | Ser | Ile | Leu | Cys | | | | | | | | | | | | |

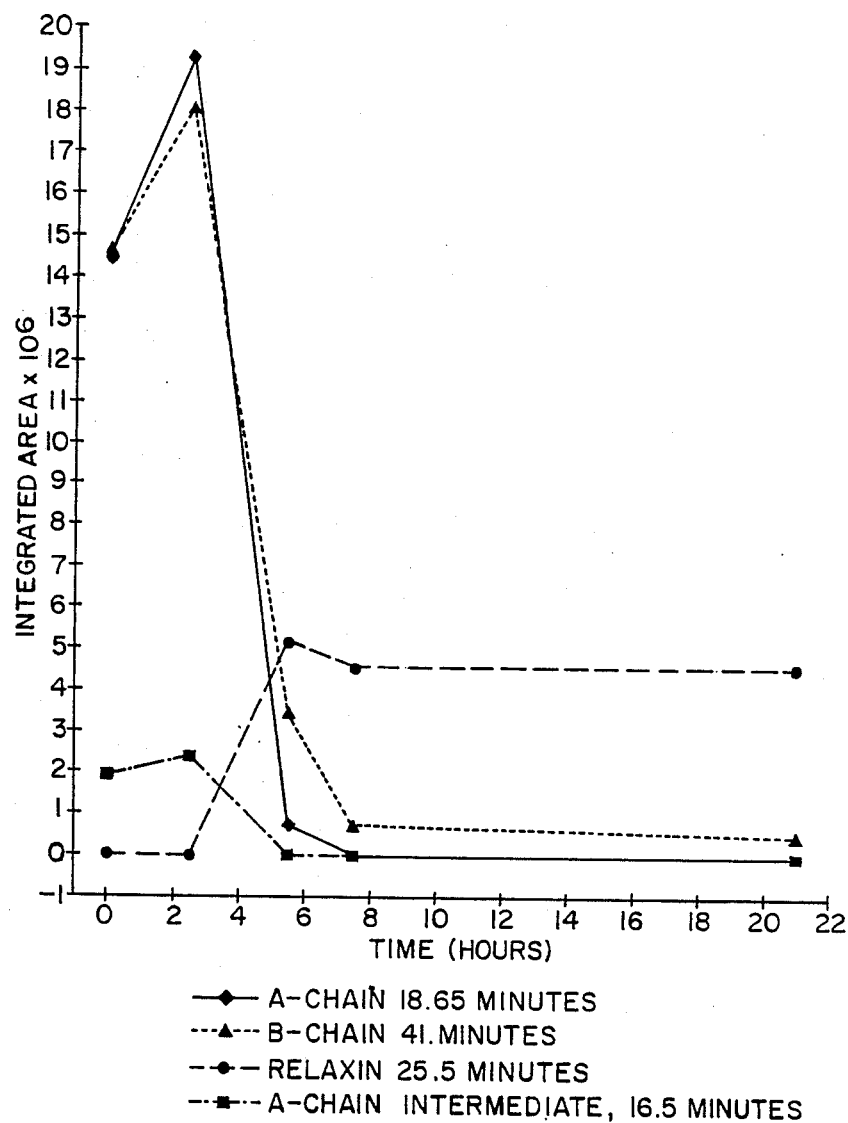

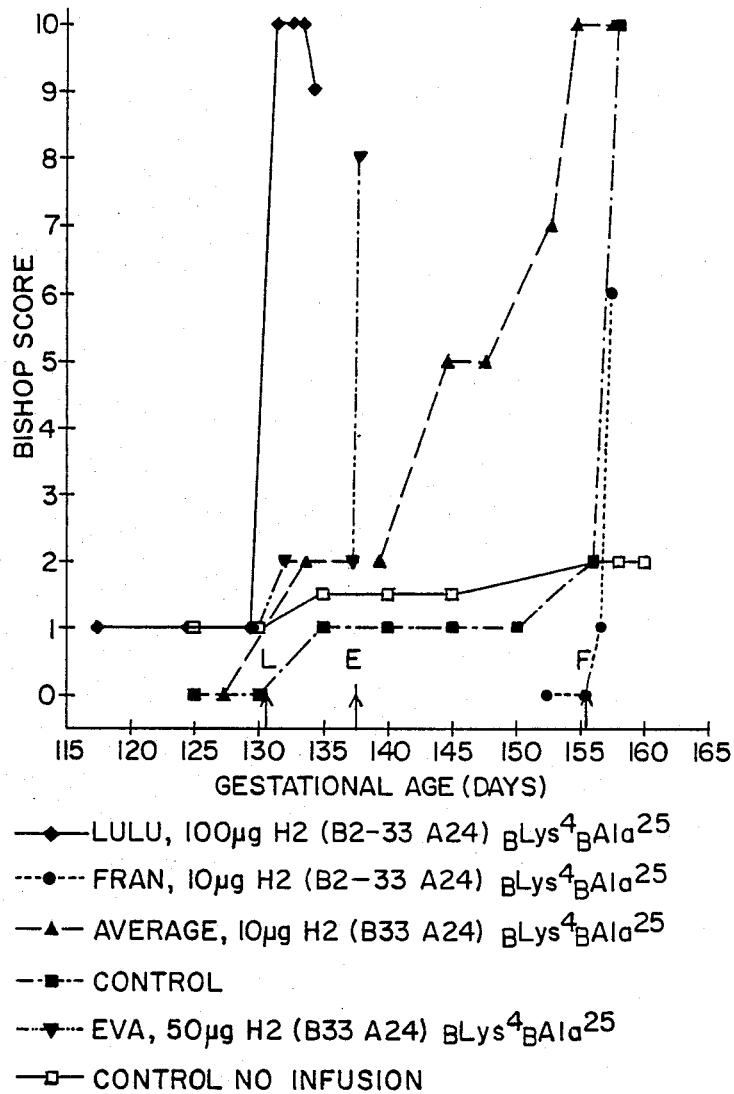

METHOD OF CHAIN COMBINATION

BACKGROUND OF THE INVENTION

This invention provides a method for the combination of human relaxin A- and B-chains or human relaxin A- and B-chain analogs to produce useful yields of biologically active human relaxin or human relaxin analog. In particular the invention comprises combining the reduced human relaxin A- and B-chains or analogs thereof under conditions which include a pH greater than about 7.0 and which are mildly denaturing with respect to the human relaxin B-chain. These conditions provide a milieu for formation of biologically active human relaxin or an analog thereof by maintaining the mixture at a temperature of from about 15° C. to 30° C. with gradual exposure to air oxygen over the course of the reaction. This invention also provides biologically active analogs of human relaxin. This invention further provides a method of effecting parturition using human relaxin or an analog thereof as the sole active agent.

Human relaxin is an ovarian peptide responsible for remodelling the reproductive tract before parturition, thus facilitating the birth process. Hisaw, F. L., Pros. Soc. Exp. Bio. Med. 23, 661-663 (1926); Schwabe, C. et al. Biochem. Biophy. Res. Comm. 75, 503-570 (1977); James, R. et al., Nature 267, 544-546 (1977). While predominantly a hormone of pregnancy, relaxin has also been detected in the non-pregnant female as well as in the male. Bryant-Greenwood, G. D., Endocrine Reviews 3, 62-90 (1982) and Weiss, G., Ann. Rev. Physio. 46, 43-52 (1984).

The amino acid sequences of relaxim from pig, rat, tiger shark, dogfish shark and human have been established. The hormone consists of two peptide chains, referred to as A and B, joined by disulfide bonds with an intro-chain disulfide loop in the A-chain in a manner analogous to that of insulin. However, a surprising and important difference between relaxin and most other peptide hormones, including insulin, is the considerable structural variation between species. For example, pig, rat and human relaxins differ in over 50% of amino acid positions. These differences explain the poor immunological cross-reactivity between relaxins of different species and also a number of the observed differences in their specific biological activity.

The application of recombinant DNA technology has led to the isolation and characterization of the genes coding for human relaxins. Hudson, P. et al., Nature 301, 628-631 (1983) and Hudson, P. et al., The EMBO Journal 3, 2333-2339 (1984). Analysis of the nucleotide sequence from cDNA and genomic clones reveals the structural organization of human relaxin to include a signal peptide of 25 residues, followed by a B-chain of about 32 to 33 amino acids, a C-peptide of about 105 amino acids, and an A-chain of 24 amino acids. In the case of human relaxin an intron interrupts the coding region of the C-peptide. The physiological role of the C-peptide, which is considerably longer than the C-peptide of insulin, and the nature of the enzymes responsible for removal of the C-peptide from the ends of the A- and B-chain are unresolved issues.

In the case of human relaxin two separate gene sequences have been identified. Id. Only one of these genes (H2) is expressed in the ovary during pregnancy, and it is unclear whether the other gene is expressed at another tissue site, or whether it represents a pseudogene. The two human relaxin genes show considerable nucleotide and amino acid homology to each other, particularly in the B and C peptide. However, there are some notable regions of sequence divergence, particularly in the amino terminal region of both A- and B-chains. See FIG. 1. The fact that H2 relaxin is synthesized and expressed in the ovary suggests that this is the sequence which is involved in the physiology of pregnancy. In a recent paper Johnston, P. D. et al., In Peptides: Structure and Function, Proc. Ninth American Peptide Symposium, Deber, C. M., Hruby, V. I. and Kopple, F. D. (eds.) (Pierce Chem Co., 1985) tested synthetic human relaxin (H2) and certain human relaxin analogs for biological activity. They defined a relaxin core necessary for biological activity as well as certain amino acid substitutions for methionine which did not affect biological activity. Id.

FIG. 1 compares the known amino acid sequences of relaxins from different species. In addition to the six cysteine residues and flanking glycine residues, only the isoleucine at position 7 in the B-chain, the arginine at positions 12 and 16, and the leucine at position 32 have been conserved. The cysteine residues are clearly essential to maintaining the overall disulfide bond configuration. Blundell, T. et al. In: Bigazzi, M., Greenwood, F. C., Gaspari, F. (eds.) Biology of Relaxin and its Role in the Human, (Excerpta Medica, Amsterdam, 1983) pp. 14-21. The species variation in the amino acid sequence at most positions in the relaxin molecule, i.e. in the A- and B-chains which comprise the active portion of the relaxin protein, is remarkable. This is in marked contrast to the situation with virtually all other peptide hormone families including insulin. Another feature of the relaxin structure is the variation in length seen at the amino and carboxyl terminal regions of the B-chain, and to a lesser extent at the amino terminus of the A-chain.

The chemical synthesis of relaxin has been particularly difficult largely as a result of the unusual solubility and structural characteristics of the isolated B-chain. Tregear, G. W. et al., In: Bigazzi, M., Greenwood, F. C. and Gaspari, F. (eds.), Biology of Relaxin and its Role in the Human, (Excerpta Medica, Amsterdam, 1983), pp. 42-55.

As discussed above human relaxin and in fact mammalian relaxin generally has some structural similarity to insulin. Both insulin and relaxin have inter-and intra-chain disulfide bonds between the two chains. James, R. et al. Nature 267; 544 (1977) and Schwabe, C. and McDonald, J. R. Science 197, 914 (1977). It was presumed that synthetic strategies which were used successfully for insulin, Busse, W. D. and Carpenter, F. J., Biochemistry 15, 1649 (1976), Katsoyannis, P. G. et al., Biochemistry 6, 2656 (1967) and Kung, Y. T. et al., Scientia Sinica 15, 544 (1966), would also be applicable to relaxin. Tregear, G. et al. In: Relaxin, G. D. Bryant-Greenwood, Niall, H. D. and Greenwood, F. C. (eds.), Elsevier, New York, 1981, attempted to synthesize relaxin using the separate chain approach using selective protection of the cysteine sulfhydryls. They found that the synthetic peptides prepared by the insulin methods had detectable relaxin-like bioactivity however, the specific activity and combination yields were very low. Id. at 151. One reason for the poor combination yields for porcine relaxin was due to the insolubility of the full length procine B-chain in solution at pH 10.5 Tregear et al., supra. modified the prior insulin combination methodology in two respects: by precipitation of the mixed porcine relaxin peptide chains with acetone to remove the reducing agent; and by adding 0.5M NaCl during the oxidation step. The results were improved yields of porcine relaxin. Also see European Patent Application No. 83.304662.6 and European Patent Application No. 83307553.4, EP Pub. Nos. 101,309 and 112,149, respectively.

Chance et al., U.S. Pat. No. 4,421,685 issued Dec. 20, 1983 disclose a method for producing insulin or an analog thereof by combining the S-sulfonated form of the insulin A- and B-chains with a thiol reducing agent in an aqueous medium under controlled pH and temperature so as to carry out the reduction and oxidation reactions in a single step. This method, while presented as an improvement over the previously mentioned insulin synthesis, was found not to be applicable to the synthesis of human relaxin.

It has now been discovered that under specific reaction conditions useful levels of human relaxin or analogs thereof can be produced by combining the reduced chains of human relaxin under controlled conditions. Thus it is an object of the present invention to provide a method for combining the A- and B-chains of human relaxin, regardless of their origin, e.g. chemical synthesis or recombinant DNA technology, to produce useful yields of biologically active human relaxin.

Another aspect of the invention is to produce biologically active analogs of human relaxin.

Yet another aspect of the invention is the use of human relaxin or an analog thereof to effect parturition.

SUMMARY OF THE INVENTION

The present invention is directed to a method of combining a human relaxin A-chain or analog thereof and a human relaxin B-chain or analog thereof to produce biologically active human relaxin or a human relaxin analog. In particular the method comprises combining the reduced human relaxin A-chain or analog and the reduced human relaxin B-chain or analog under conditions which include a pH greater than about 7.0, that is mildly denaturing with respect to the human relaxin B-chain and carrying out the reaction with gradual exposure to air oxygen over the course of the reaction.

BRIEF DESCRIPTION OF THE DRAWINGS

FIG. 1 shows the lack of homology of human relaxin H1 and H2 with human insulin and procine (P) and rat (R) relaxins. The numbering system is relative to H2 relaxin. The disulfides for the relaxins are: A10-A15, A11-B11 and A24-B23.

FIG. 4 shows the modified Bishop score in primate following administration of various doses of human relaxin analogs, H2(B2-33 A24) $_B$Lys$^4$ $_B$Ala$^{25}$ and H2(B33 A24) $_B$Lys$^4$ $_B$Ala$^{25}$.

DETAILED DESCRIPTION

Figure 2A:
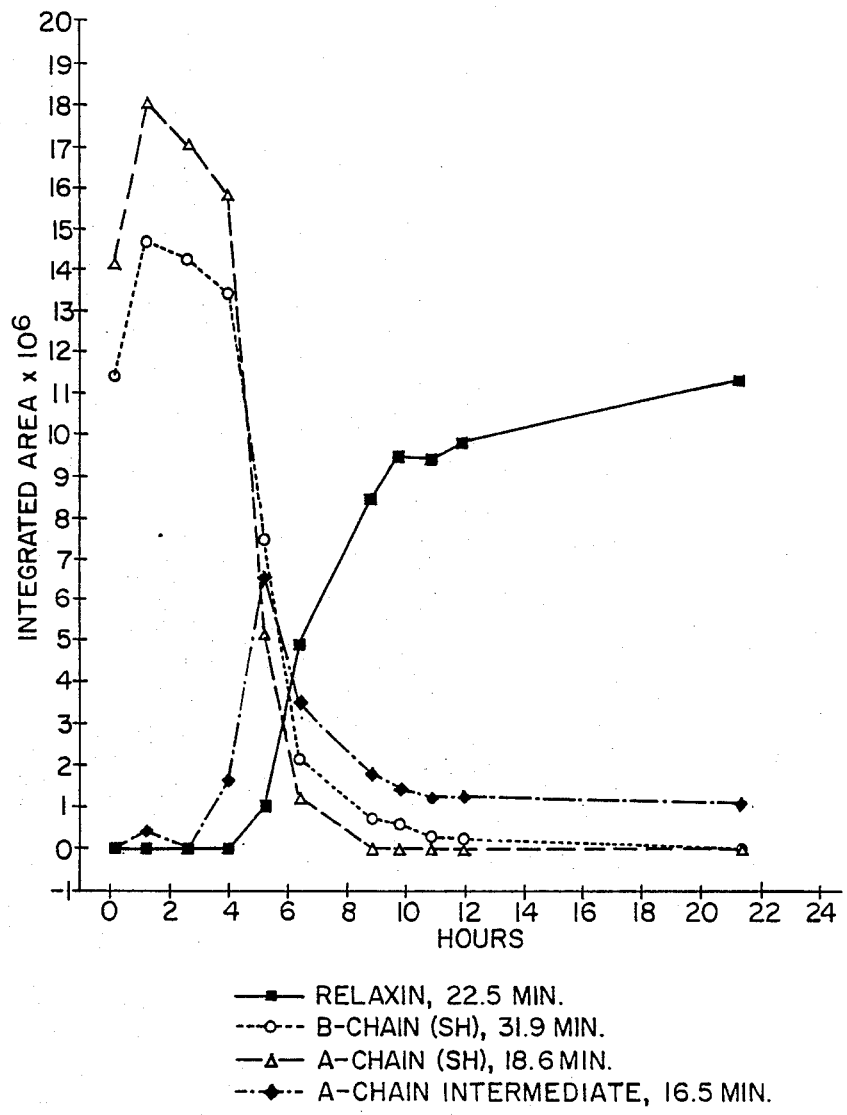
FIG. 2(a) shows the HPLC time course for H2(B33 A24) $_B$Lys$^4$ $_B$Ala$^{25}$ and FIG. 2(b) for H2(B33 A24) profile of the in vitro chain combination reaction. The time course of the combination reaction showing the formation of human relaxin analog or human relaxin and a potentially important intramolecular oxidized intermediate of the A-chain is described. The conversion of gene-2 A- and B-chain peptides to H2 human relaxin analog and H2 human relaxin is delineated.. Chromatography is effected using a Synchropak RP-C4 (4.6×250 mm; 300 Å) with a linear gradient of acetonitrile (15→60% in 500 minutes) in a 0.05% TFA, H20 buffer running at 1 ml/min.

As used herein "human relaxin" or "human relaxin analog" refers to a functional protein that is known to remodel the reproductive tract to facilitate the birth process. Remodeling of the reproductive tract is understood to include such physiological actions as ripening of the cervix; thickening of the endometrium of the pregnant uterus as well as increased vascularization to this area; and, an effect on collagen synthesis. Human relaxin has also been found in the female breast and may be associated with lactation. Human relaxin has also been found in human seminal fluid and may enhance the mobility of human spermatozoa. Given the effect of relaxin on the cervix human relaxin may augment the ability of sperm to penetrate the human cervix. Human relaxin may improve skin elasticity given its effect on connective tissue.

Human relaxin analog in addition to the functional definition described above structurally is meant to include a number of proteins, each of which has the basic structure of human relaxin including an A- and B-chain. The human relaxin analog differs from the naturally occurring human relaxin by substitution, deletion, addition or modification of one or more amino acid residues in either the A- and/or B-chain of human relaxin with the caveat that biological relaxin-like activity is retained. Examples of such human relaxin analogs include, but are not limited to: a full length A-chain and carboxy terminal shortened B-chain; H1(B2-27 A24) $_B$Ala$^{25}$; H2(B2-25 A24); H2(B33 A24); H2(B33 A24) $_B$Lys$^4$ $_B$Ala$^{25}$; H2 (B2-33 A24) $_B$Lys$^4$ $_B$Ala$^{25}$; H2(B2-33 A24) $_A$pyro-Glu$^1$ $_B$Lys$^4$ $_B$Ala$^{25}$; and H2(B33 A24) $_A$pyro-Glu$^1$ $_B$Lys$^4$ $_B$Ala$^{25}$. The nomenclature is as follows: H1, H2 refer to the two human genes which encode human relaxin. H2 has been found to be expressed in the human ovary while H1 has only been found as a genomic clone. A and B refer to the respective chains of human relaxin. The numbers following A or B refer to the length of the chain, i.e. number of amino acids comprising the A- or B-chain. Amino acids are designated by their customary three letter notation. The subscript preceding the amino acid designates the A- or B-chain in which the amino acid is located while the superscript following the amino acid refers to the position in the chain.

The relaxin A- and B-chains or analog chains may be obtained by classical protein synthetic methods, including either solution or solid phase techniques, or using recombinant DNA technology or by preparation from natural human relaxin or a combination of the above, e.g., chemical synthesis of one chain and recombinant DNA production of the other. The individual peptide chains were synthesized via solid phase synthetic methodology, Barany, G. and Merrifield, R. B. (1980) in The Peptides 2, 1–284. Gross, E. and Meienhofer, J. Eds. Academic Press, New York. Protected N-t-butyloxycarbonyl amino acids were purchased from Peninsula Laboratories Inc. The following side chain protection was used; Arg, tosyl; Asn, xanthyl; Asp, benzyl ester; Cys, methoxybenzyl; Gln, xanthyl; Glu, benzyl ester; His, tosyl; Lys, o-chlorobenzyloxycarbonyl; Ser, benzyl; Thr, benzyl; Tyr, 2,6-dichlorobenzyl. The first amino acids were esterified onto chloromethylpolystyrene (1% divinylbenzene) with potassium fluoride in dimethylformamide. Substitution levels were 0.6 meq/gm. The amino acids were coupled with dicyclohexylcarbodiimide (distilled) in dichloromethane. Arginine, asparagine, glutamine, leucine, and cysteine residues were coupled in 50/50 methylenechloride/dimethylformamide. Removal of the t-butyloxycarbonyl groups was accomplished with 45% trifluoroacetic acid, 5% anisole 5% ethanedithiol, and 45% methylenechloride. Neutralization prior to couplings was done with 10% triethylamine in methylenechloride. Cleavage from the resin and removal of all the protecting groups was accomplished by treatment with anhydrous liquid hydrogen fluoride in the presence of anisole and methylethylsulfide (20:3:1 v/v/v) at 0° C. for one hour. Crude A-chain was removed from the resin with 10% aqueous acetic acid and lyophilized. Crude B-chain was removed from the resin by washing first with 80% aqueous acetonitrile and then 30% aqueous acetic acid followed by dilution with water and lyophilization. The crude peptides were dissolved in 100 mmol dithiothreitol and then diluted into a large volume of 10% aqueous acetonitrile 0.1% trifluoroacetic acid. These solutions were loaded onto 5×55 cm columns packed with Vydac C18 (300 Å 15–20 micron), washed with 0.1% aqueous trifluoroacetic acid, and eluted with a gradient of acetonitrile. The peptide fractions were pooled, lyophilized, and analyzed by amino acid composition, sequencing and analytical reverse phase HPLC. The cysteine residues were not protected by sulfonation or other derivatizations, Means, G. E. and Feeney, R. E., *Chemical Modification of Proteins* (1971), as was the case with the prior isulin or porcine relaxin methodology. Improved yields and peptide solubility are obtained according to the method of the instant invention by keeping the human relaxin A- and B-chains in their reduced form. The reduced and lyophilized A- and B-chains were used directly for all recombination reactions without conversion to the sulfonated derivative or use of other cystine thiol blocking agents.

In carrying out the process of this invention, the combination of human relaxin A- and B-chain or analog A- and B-chain to form human relaxin or a human relaxin analog can be achieved over a wide range of ratios of one chain relative to the other. The combination, of course, is inherently limited by the chain, whether A or B, present in the lesser quantity. Excess B-chain, inhibits chain combination, while molar amounts of A-chain either in a slight excess or equal to B-chain are preferable. In any event, although not essential, the customary ratio of A-chain to B-chain, on a weight basis, is from about 1:0.5 to about 3.0:1. It is highly preferred to carry out the process of this invention using a weight ratio of A-chain to B-chain in the range from about 1:1 to about 2.5:1. It has also been discovered, within this preferred range, that certain ranges are especially advantageous for production of a particular relaxin analog. Thus, in the combination of human relaxin A- and B-chain to produce desmethionine relaxin it is preferred that the ratio of A-chain to B-chain be within the range of from about 1.2:1 to about 2:1.

Another parameter which is significant for carrying out the process of this invention at an optimal level is the protein concentration in the reaction medium. The process can be successfully carried out over a wide range of protein concentrations. Generally, however, the protein concentration will range from about 0.1 to about 10 mg. per ml. of reaction medium. Preferably, the protein concentration will be in the range of from about 0.5 to about 5 mg.per ml. Again, it has been discovered, within this latter range, that the optimal protein concentration varies depending upon the human relaxin produced.

The process of this invention is carried out in an aqueous medium. The pH of the medium measured at room temperature generally will range from about 7.0 to about 12. Preferably, it will be from about 7.5 to about 11.0 and optimally will be maintained within the range of from about 8.0 to about 10.6. The pH of the medium may be maintained in the desired range by addition of a suitable suffering agent. Typical buffering agents are, for example, glycinate, carbonate, tris (hydroxymethyl) aminomethane, pyrophosphate and other like agents which affect pH control within the aforedescribed range. The common and preferred buffering agent is tris (hydroxymethyl) aminomethane (pH 8 to 9) and glycinate (pH 9.5 to 11.0).

The mixing reaction is carried out at a temperature of from about 15° C. to about 30° C. and preferably from about 20° C. to about 25° C. and most preferably at room temperature.

The concentration of buffering agent generally ranges from about 0.025M to about 0.2M. Preferably, the concentration is from about 0.05M to about 0.15M, and, most preferably about 0.1M.

One of the conditions of the inventive method is that it be carried out in an environment in which the exposure to air oxygen may be controlled. It was found that controlled oxidation could be achieved by $N_2$ purge of all solutions initially; that the reaction be $N_2$ purged in a closed container at the start of the reaction; and that while in a closed container the reaction be exposed to air directly by opening of the container or to oxygen by bubbling it into and through the medium.

Another condition of the inventive method is that the reaction be carried out under such conditions as to be mildly denaturing with respect to the human relaxin B-chain. Such denaturing agents as urea, guanidine hydrochloride and other chaotropic agents, salts, detergents and organic solvent (acetonitrile, alcohols, dimethylformamide, etc.) known to the ordinarily skilled artisan could be used. Preferably urea and acetonitrile and a few percent based on volume (less than 10%) of organic solvents render the conditions mildly denaturing to the human relaxin B-chain.

The human relaxin A- and B-chains are brought together in the appropriate aqueous medium in free-cysteine reduced forms. The reactions were started by first adding A-chain followed by B-chain from fresh 5 mg/ml stocks in $H_2O$ at pH2. The pH is adjusted to the appropriate value with NaOH. Each reaction is monitored by RP-4 reverse phase analytical HPLC Snyder, L. R. and Kirkland, J. J. in *Introduction to Modern Liquid Chromatography* (1979), for maximal formation of recombined relaxin and stopped by addition of glacial acetic acid to pH 4. The mixture is then centrifuged at 16,318×g for 30 minutes and the supernatant purified by preparative reverse phase HPLC. Id. It was observed that carrying out the combination reaction at room temperature was important to produce usable yields of human relaxin. High performance liquid chromatography analytical work was done using Synchropak RP-4 (4.6×250 mm, 300 Å) reverse phase column. Preparative work was done using either Synchropak RP-4 (1×50 cm, 300 Å) or hand packed Vydac RP-4 or RP-18 (5×50 cm), 300 Å reverse phase columns. Analytical HPLC was done using a Water's System. Preparative HPLC was done using Water's System or Prep 500.

Once the reaction period has been completed, the human relaxin or relaxin analog product can be isolated by any of a wide variety of methods, all of which are recognized in the field of protein isolation. The most commonly employed techniques for relaxin purification are chromatographic techniques. These are readily applicable in recovering human relaxin from the process of this invention. These can include gel filtration, ion-exchange chromatography or reverse phase HPLC.

An example of a purification scheme was to load the reaction supernatants totaling 0.5 to 1 gram of relaxin peptide on a (15–20 micron) Vydac C4 300 Å (5×50 cm) column. Purification was achieved using a 20 to 40% acetonitrile gradient (0.5% change per minute) in $H_2O$, 0.1% TFA. The flow rate was 20 ml/min and 1.0 minute fractions were collected. These were monitored isocratically 25% acetonitrile, $H_2O$, 0.1% TFA on an analytical (5 micron) Vydac C4 300 Å (4.6×250 mm) column. Fractions containing major products were pooled and lyophilized for further analysis.

The human relaxin and human relaxin analogs were tested in bioassays. The murine pubic symphysis assay (MPS) uses Charles River albino CFW female mice weighing 18–20 g., J. St. Louis, Can. J. Physiol. Pharmacol. 59, 507–512 (1981). Estradiol priming solution is 5 $\mu$g estradiol 17$\beta$-cyclopentylpropionate in 0.1 ml peanut oil. Human relaxin dose solutions are at concentrations of 2.5, 5.0, 10.0, 20.0, 40.0, and 80.0 $\mu$g/ml in a 1% water solution of benzopurpurine 4B. When mice have been housed for at least six days in quarantine and weigh 18–20 g, each one is given a subcutaneous injection of estradiol priming solution. Exactly seven days later mice are injected subcutaneously with 0.2 ml of the appropriate human relaxin dose solution. Between 18 and 20 hours after the human relaxin injection the mice were sacrificed by cervical dislocation. The interpubic ligament is exposed and measured with a micrometer.

Charles River albino Sprague-Dawley derived female rats weighing 200–300 grams are used for the rat uterine contractility assay (RUC). Estradiol priming solution is 200 $\mu$g estradoil 17$\beta$-cyclopentylpropionate in 0.1 ml peanut oil. Human relaxin stock solution is at a concentration of 0.1 mg/ml in sterile injection water (Invenex). When rats have been housed for at least six days in quarantine each is given a subcutaneous injection of estradiol priming solution. Between 16 and 20 hours after the estradoil injection the rats are sacrificed by carbon dioxide asphyxiation. The uteri are dissected out, the horns split and divided laterally, four pieces of uteri per animal. Each tissue is suspended in a jacketed water bath kept at 37° C. containing 35 ml of aerated Holmans Ringer Solution. The tissue is caused to contract by replacing the Ringer solution with one in which 20 percent of the sodium chloride is replaced with an equimolar amount of potassium chloride. After a steady plateau is reached a concentration of relaxin is added to the bath. For the standard curve, doses of porcine relaxin added to the bath are 0.2, 0.4, 0.8, 1.6, 3.2, 6.4, and 12.8 $\mu$g relaxin per 35 ml in the bath.

Human relaxin's induction of cervical ripening in a nonhuman primate pregnancy was tested. Human relaxin was tested in time-mated Rhesus monkeys at gestational ages from 130 to 160 days. Term gestation in the colony is 168±6 days. The animals were adapted to wearing jackets with tethers. The tethered jackets permitted continuous access to indwelling catheters placed either in the femoral vessels or in the carotid and internal jugular vessels. In most animals a pressure transducer was placed within the amniotic sac and electrodes connected to the uterine surface allowing measurement of uterine contractile activity. Relaxin was administered as a continuous IV infusion over one hour, with blood samples obtained before, during and after the infusion at intervals from 15 minutes through the first hour following the infusion and then regularly for 24 hours. Doses of relaxin ranged from 10 $\mu$g to 100 $\mu$g, and the cervix was scored for texture, effacement, position, dilation, and fetal position relative to the cervix, as well as the quality of the uterine lower segment. In most cases, two observers examined each cervix and scored them independently. Controls were monkeys operated upon in similar manner and infused with saline (one) or monkeys maintained in the colony but not operated upon with cervical exams performed at weekly intervals.

Western blots and urea polyacrylamide gel electrophoresis to isolate protein were performed. Low molecular weight 15% polyacrylaamide, urea, slab gels following the procedure given by Bethesda Research Laboratories in their brochure for molecular weight standards. Some modifications of that procedure have been used. The gels are run in the cold room, 4° C., for 15 hours at 100 constant voltage. Samples are prepared in 10mM sodiumphosphate, pH 7.2, 7M urea, 0.01% bromophenol blue, and for reduced samples 50mM freshly prepared DTT. From 1 to 10 $\mu$g total peptide is incubated at 90° C. for 2–3 minutes prior to loading. The gels are incubated at 90° C. for 2–3 minutes prior to loading. The gels are visualized by Coomassie Blue (gel soaked 1.5 hrs in 10ml acetic acid plus 90ml (0.25% weight/volume) Coomassie Blue R-250 in 25% ethanol), silver stain (Oakley, B. R. et al. Analytical Biochem. (1980) 105, 361–363), after fixing and destaining in a solution of 0.2% formaldehyde, 20% ethanol, and 6.2% acetic acid (all volume/volume) for 15–30 minutes and Western analysis (Towbin, H. et al. PNAS (1979) 76; 4350–4354).

Antibodies specific for the A- and B-chains were raised by immunizing New Zealand white rabbits with the free peptides either alum precipitated or in Freund's adjuvant as described in Eddie, L. W. et al. (1986) The lancet 1, 1344–1346. The titers were essentially the same and antisera from each immunization was pooled with bb titer for the A-chain and ccc titer for the B-chain. These were used at 500 fold dilution in the incubation against the nitrocellulose filters 2 hours to overnight. The washed filters are then incubated against 125I-protein A for 2 hours, dried and placed against X-ray film.

As illustrative of the inventive method the following examples are provided. These examples are set forth for illustrative purposes only and are not intended to be limiting upon the scope of this invention.

EXAMPLE 1

Natural Human Relaxin

H2(B33 A24)

Reduced relaxin A-chain (10 mg) was added as a reduced solid lyophilized powder to the reaction mixture. Reduced relaxin B-chain (5.63 mg) was also added as a solid lyophilized powder.

The A and B relaxin chain solutions were combined in a 10 ml vial at room temperature ($\sim$25° C.) by first adding the relaxin A-chain followed by relaxin B-chain as solid lyophilized powders from above. The pH was adjusted to 10.5 using NaOH. The reaction was monitored by RP-4 reverse phase analytical HPLC for maximal formation of recombined relaxin. Due to the insolubility of the natural form of H2 B-chain, its recombination with A-chain required the following conditions in accord with the invention; final reaction 0.1M glycine, pH 10.5, 1mM EDTA, 2.5mM DTT, 3% 1-propanol, 3% acetonitrile, and 1M urea. The reaction was stirred open to air for 28 hours at room temperature. Relaxin formation was monitored by analytical reverse phase HPLC and stopped as described above. Analysis by high performance liquid chromatography (HPLC) indicated a relaxin yield of 1.87 mg, or 19.5% incorporation of B-chain.

The mixture was purified by preparative RP-4 reserve phase HPLC (1×25cm) RP-4 Synchropak 300 A. The peak was pooled and used directly out of HPLC solvent. The human relaxin was judged to be quite pure by polyacrylamide gel electrophoresis, amino acid analysis HPLC, amino terminal sequencing and bioassay.

EXAMPLE 2

Human Relaxin Analog

H2(B 33 A24) $_B$Lys$^4$ $_B$Ala$^{25}$

Reduced human relaxin A-chain (200 mg) was dissolved in 40 ml of H$_2$O (pH 2.0). Reduced human relaxin B-chain (B33 $_B$Lys$^4$ Ala$^{25}$) (100 mg) was dissolved in 20 ml of H$_2$O (pH 2).

The A- and B-chain analog solutions were combined in a 165 ml vial at room temperature (~25° C.) by first adding the A-chain followed by modified B-chain from the foregoing fresh stocks in H$_2$O, pH2. The pH was adjusted to about 8.0 with NaOH. The reaction was monitored by RP-4 reverse phase HPLC for maximal formation of combined human relaxin analog. For this human relaxin analog the following conditions in accord with the instant invention were used; reaction B 0.1M tris, pH 8.0, 1 mM EDTA, 2 mM DTT, 24° C. The reaction was stirred vigorously open to the air. The combination reaction was stopped by addition of glacial acetic acid to pH 4.

The mixture was purified by preparative HPLC Vydac C4 300 Å (5×50 cm). The human relaxin analog peak (elution volume, about 140 ml) was pooled and lyophilized with a recovery of 35 mg of relaxin, or 20.3% incorporation of B-chain. The human relaxin analog was judged to be quite pure by polyacrylamide gel electrophoresis, amino acid analysis, amino terminal sequencing, HPLC (see FIG. 2a.) and the bioassay.

EXAMPLE 3

Human Relaxin Analog

H2(B2-33 A24) $_B$Lys$^4$ $_B$Ala$^{25}$

Reduced human relaxin A-chain (41.5 mg) was dissolved in 8 ml of H$_2$O (pH 2.0). Reduced human relaxin B-chain (B2-33 $_B$Lys$^4$ $_B$Ala$^{25}$) (23 mg) with the first amino acid deleted from the amino terminus was dissolved in 4 ml of H$_2$O (pH 2).

The A- and B-chain analog solutions were combined in a 33 ml vial at room temperature (~25° C.) by first adding the A-chain followed by modified B-chain from the foregoing fresh stocks in H$_2$O, pH2. The pH was adjusted to 8.0 with NaOH. The reaction was monitored by RP-4 reverse phase HPLC for maximal formation of combined human relaxin analog. For this relaxin analogue the following conditions in accord with the instant invention were used: reaction D 0.1M Tris, pH 8, 25° C.; purged with N$_2$ and stirred under N$_2$ atmosphere for the first 1-2 hours. The reaction was then stirred vigorously open to the air. The combination reaction was stopped by addition of glacial acetic acid to pH4.

The mixture was purified by preparative HPLC Vydac C4 300 Å (5×80 cm). The relaxin analog peak (elution volume, about 140 ml) was pooled and lyophilized with a recovery of 16 mg of human relaxin analog, or 40.3% incorporation of B-chain. The relaxin analog was judged to be quite pure by polyacrylamide gel electrophoresis, amino acid analysis, amino terminal sequencing, HPLC (see FIG. 2a.) and the bioassay.

EXAMPLE 4

Human Relaxin Analog

H2(B2-33 A24)$_A$pyro-Glu$^1$ $_B$Lys$^4$ $_B$Ala$^{25}$

Reduced human relaxin A-chain (41.5) was dissolved in 8 ml of H$_2$O (pH 2.0). Reduced human relaxin B-chain (B2-33 $_B$Lys$^4$ $_B$Ala$^{25}$) (23 mg) with the first amino acid deleted from the amino terminus was dissolved in 4 ml of H$_2$O (pH 2).

The A- and B-chain analog solutions were combined in a 33 ml vial at room temperature (~25° C.) by first adding the A-chain followed by modified B-chain from the foregoing fresh stocks in H$_2$O, pH2. The pH was adjusted to 8.0 with NaOH. The reaction was monitored by RP-4 reverse phase HPLC for maximal formation of combined human relaxin analog. For this relaxin analogue the following conditions in accord with the instant invention were used: reaction D 0.1M Tris, pH 8, 25° C.; purged with N$_2$ and stirred under N$_2$ atmosphere for the first 1-2 hours. The reaction was then stirred vigorously open to the air. The combination reaction was stopped by addition of glacial acetic acid to pH4.

The mixture was purified by preparative HPLC Vydac C4 300 Å (5×80 cm). The relaxin analog peak (elution volume, about 140 ml) was pooled and lyophilized with a recovery of 7.5 mg of human relaxin analog, or 18.9% incorporation of B-chain. The relaxin analog was judged to be quite pure by polyacrylamide gel electrophoresis, amino acid analysis, amino terminal sequencing, HPLC (see FIG. 2a.) and the bioassay.

EXAMPLE 5

Human Relaxin Analog

H2(B33 A24)$_A$pyro-Glu$^1$ $_B$Lys$^4$ $_B$Ala$^{25}$

Reduced human relaxin A-chain (200 mg) was dissolved in 40 ml of H$_2$O (pH 2.0). Reduced human relaxin B-chain (B33 $_B$Lys$^4$ $_B$Ala$^{25}$) (100 mg) was dissolved in 20 ml of H$_2$O (pH 2).

The A- and B-chain analog solutions were combined in a 165 ml vial at room temperature (~25° C.) by first adding the A-chain followed by modified B-chain from the foregoing fresh stocks in H$_2$O, pH2. The pH was adjusted to about 8.0 with NaOH. The reaction was monitored by RP-4 reverse phase HPLC for maximal formation of combined human relaxin analog. For this human relaxin analog the following conditions in accord with the instant invention were used: reaction B 0.1M sodium glycinate, pH 8.0, 1 mM EDTA, 2 mM DTT, 24° C. The reaction was stirred vigorously open to the air. The combination reaction was stopped by addition of glacial acetic acid to pH4.

The mixture was purified by preparative HPLC Vydac C4 300 Å (5×50 cm). The human relaxin analog peak (elution volume, about 140 ml) was pooled and lyophilized with a recovery of 16 mg of relaxin, or 9.3% incorporation of B-chain. The human relaxin analog was judged to be quite pure by polyacrylamide gel electrophoresis, amino acid analysis, amino terminal sequencing, HPLC (see FIG. 2a.) and the bioassay.

EXAMPLE 6

Biological Assays

Figure 3:
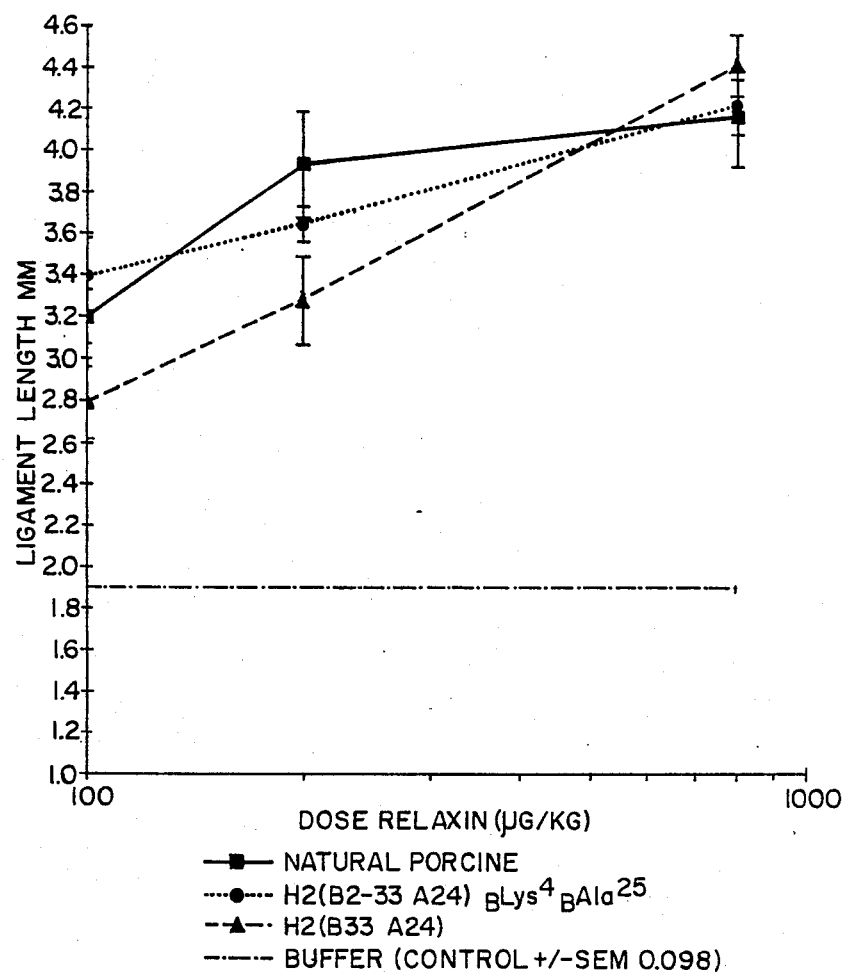
FIG. 3 shows the bioactivity (MPS) of chain-combined human gene-2 relaxin H2(B2-33 A24) $_B$Lys$^4$ $_B$Ala$^{25}$ and natural human relaxin.

The rat uterine contractility in vitro bioassay measures human relaxin ability to relax smooth muscle in the presence of electrically stimulated contractions, J. St. Louis, (1981) Can. J. Physiol. Pharmacol. 59, 507–512. The murine pubic symphysis ligament in vivo bioassay measures relaxin's remodeling effect on connective tissue, Steinetz, B. G. et al. (1960) Endocrinology 67, 102. Biological dose response comparisons of H2(B2-33 A24), H2(B32 A24) $_B$Lys$^4$ $_B$Ala$^{25}$, H2(B33 A24) $_B$Lys$^4$ $_B$Ala$^{25}$, and the pyro-Glu forms of the foregoing H2(B2-33 A24) $_B$Lys$^4$ $_B$Ala$^{25}$ $_A$pyro-Glu$^1$ and H2(B33 A24) $_B$Lys$^4$ $_B$Ala$^{25}$ $_A$pyro-Glu$^1$ indicated biological activity in both the MPS and RUC assays. The MPS data for a human relaxin analog and human relaxin is shown in FIG. 3. The MPS does responses indicate equipotence for natural human relaxin and H2(B2-33 A24) $_B$Lys$^4$ $_B$Ala$^{25}$, FIG. 3. However, porcine relaxin appears to have a non-parallel response relative to the other relaxins. All of the human analogues and natural sequence human relaxin are essentially indistinguishable in the MPS bioassay.

Because of the amount of purified H2(B33 A24) available it could only be compared at the high end of the dose range. The results establish the similarity of activity for the native human relaxin and the analog forms of human relaxin. The slope of the human relaxin dose response curve may differ from that of the analogs.

In the RUC bioassay the slopes of human relaxin and the human relaxin analogs are identical.

EXAMPLE 7

Human Relaxin in Primate Pregnancy

Two human relaxin analogs H2(B33 A24) $_B$Lys$^4$ $_B$Ala$^{25}$ and H2(B2-33 A24) $_B$Lys$^4$ $_B$Ala$^{25}$ have been tested in time-mated Rhesus monkeys at gestational ages from 130 to 160 days using the methodology described above.

Using a modified Bishop's score for the parameters observed, the mean cervical change for 7 separate infusions of various doses was 3.7 units. These data are presented in FIG. 5, where the individual infusions at 100, 50 and 10 μg doses are shown, as well as an average of all other 10 μg infusions and the two kinds of controls. Note the non-infused control monkeys range from 2 to 15 determinations per point (except for two points each is representative of at least 4 monkeys, and the mean is plotted. In general, the cervix was more sensitive to lower doses of relaxin as gestation progressed, or to repeated administration of relaxin early in this time period. High doses of relaxin (100 or 50 μg) were able to effect significant changes in cervical ripening (inducing a change of 1 to 10 in score) even at relatively early time periods in gestation (130–140d). The cervical changes appeared to occur independent of any consistent change in uterine electromyographic activity or intrauterine pressure. These results indicate that combined human relaxin is highly effective in causing cervical ripening in primates during the last third of gestation.

The human relaxin and human relaxin analogs of the present invention can be formulated using known methods to prepare pharmaceutically useful compositions such that the human relaxin or analog thereof is combined with a pharmaceutically acceptable carrier. Suitable vehicles and their formulation, including other necessary human proteins, e.g., human serum albumin, are described in standard formulation treatises e.g. Remington's *Pharmaceutical Sciences* by E. W. Martin.

I claim:

1. A method for combining an A-chain of human relaxin and a B-chain of human relaxin to produce biologically active human relaxin product, which comprises mixing the reduced, free-cysteine form of the A-chain and the reduced, free-cysteine form of the B-chain in an aqueous medium having a pH of from about 7.0 to 12 under exposure to oxygen, under conditions whereby the B-chain, but not the relaxin product, is denatured.

2. The method of claim 1 in which the reduced form of the human relaxin A-chain and the reduced form of the human relaxin B-chain each has the amino acid sequence represented by naturally occurring human relaxin (H2).

3. The method of claim 1 in which the reduced form of the human relaxin A-chain and the reduced form of the human relaxin B-chain each has the amino acid sequence represented by naturally occurring human relaxin (H1).

4. The method of claim 1 wherein said mixing is conducted at a temperature of from about 15° C. to about 30° C.

5. The method of claim 1 wherein said mixing is conducted at room temperature.

6. The method of claim 1 wherein the molar amount of relaxin A-chain is equal to or in excess of the molar amount of relaxin B-chain.

7. The method of claim 1 wherein the ratio of the relaxin A-chain to relaxin B-chain is about 1:0.5 to 3.0:1 on a weight basis.

8. The method of claim 1 wherein the ratio of the relaxin A-chain to relaxin B-chain is about 1:1 to 2.5:1 on a weight basis.

9. The method of claim 1 wherein the relaxin concentration ranges from about 0.1 to 10 mg per ml. of reaction medium.

10. The method of claim 1 wherein the relaxin concentration ranges from about 0.5 to 5 mg per ml. of reaction medium.

11. The method of claim 1 wherein the mixing takes place in the presence of a denaturing agent.

12. The method of claim 11 wherein the denaturing agent is a chaotropic agent or an organic solvent or a mixture thereof.

13. The method of claim 12 wherein the chaotropic agent is urea or guanidine hydrochloride and the organic solvent is acetonitrile, an alcohol, or dimethylformamide.

14. The method of claim 13 wherein the chaotropic agent is urea and the organic solvent is acetonitrile or 1-propanol or both in an amount based on volume of less than 10%.

15. The method of claim 1 wherein the mixing takes place at a temperature of at least about 15° C.

16. A method for combining an A-chain of human relaxin or analog thereof with a pyro-Glu at position 1 and a B-chain human relaxin analog having from 25 to 33 amino acids, wherein if the B-chain analog has 33 amino acids at least one methionine in said chain is substituted with another amino acid, to produce biologically active human relaxin product, which comprises mixing the reduced, free-cysteine form of the A-chain and the reduced, free-cysteine form of the B-chain in an aqueous medium having a pH of from about 7.0 to 12 under exposure to oxygen.

17. The method of claim 16 in which the reduced form of the human relaxin A-chain has a pyro-Glu at position 1 of said chain.

18. The method of claim 16 wherein the mixing takes place at a temperature of at least about 15° C.

19. The method of claim 16 in which the reduced form of the human relaxin B-chain has at least twenty-five and up to and including thirty-two amino acids with a substitution for at least one methionine in said chain.

20. The method of claim 19 in which the reduced form of the human relaxin B-chain is shortened to thirty-two amino acids with a lysine at position 4 and alanine at position 25 of said chain.

* * * * *